US008328983B2

(12) United States Patent
Tan et al.

(10) Patent No.: US 8,328,983 B2
(45) Date of Patent: *Dec. 11, 2012

(54) MODIFIED KRAFT FIBERS

(75) Inventors: Zheng Tan, Mason, OH (US); Gopal Goyal, Mason, OH (US); Alexander A Koukoulas, Walpole, MA (US)

(73) Assignee: International Paper Company, Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/439,659

(22) Filed: May 24, 2006

(65) Prior Publication Data

US 2007/0000627 A1   Jan. 4, 2007

Related U.S. Application Data

(60) Provisional application No. 60/684,018, filed on May 24, 2005.

(51) Int. Cl.
*D21C 3/26* (2006.01)
(52) U.S. Cl. .................. 162/37; 162/17; 162/19
(58) Field of Classification Search .................. 162/82, 162/68, 63, 72, 17, 19, 37
See application file for complete search history.

(56) References Cited

U.S. PATENT DOCUMENTS

| | | | |
|---|---|---|---|
| 1,831,032 A * | 11/1931 | Richter | 162/65 |
| 2,709,699 A | 5/1955 | Wolf | |
| 2,801,955 A * | 8/1957 | Rutenberg et al. | 435/277 |
| 2,904,460 A * | 9/1959 | Nolan | 162/25 |
| 3,617,431 A | 11/1971 | Croon et al. | |
| 3,932,209 A * | 1/1976 | Chatterjee | 162/157.6 |
| 4,174,997 A | 11/1979 | Richter | |
| 4,436,586 A | 3/1984 | Elmore | |
| 4,475,984 A | 10/1984 | Cael | |
| 4,486,267 A | 12/1984 | Prusas | |
| 4,557,800 A | 12/1985 | Kinsley, Jr. | |
| 4,668,340 A | 5/1987 | Sherman | |
| 4,806,203 A | 2/1989 | Elton | |
| 4,997,488 A | 3/1991 | Gould et al. | |
| 5,531,728 A | 7/1996 | Lash | |
| 5,589,033 A * | 12/1996 | Tikka et al. | 162/84 |
| 5,676,795 A | 10/1997 | Wizani et al. | |

(Continued)

FOREIGN PATENT DOCUMENTS

CA      2036311      8/1991

(Continued)

OTHER PUBLICATIONS

Gullichsen J. Editor, Chemicial Pulping, 1999, Fapet Oy., p. A25-A28.*

(Continued)

*Primary Examiner* — Anthony Calandra
(74) *Attorney, Agent, or Firm* — Thomas W. Barnes, III; Matthew M. Eslami; Eric W. Guttag

(57) ABSTRACT

A method of producing a modified pulp for use in paper or paper web products, the method comprising treating wood chips in an extraction process to remove hemicellose to form treated wood chips; and subjecting said treated wood chips to chemical or semichemical pulping to form a modified Kraft pulp wherein the amount of hemicellulose contained in the modified Kraft pulp is from about 5 to about 10% by dry weight of the modified pulp.

17 Claims, 2 Drawing Sheets

U.S. PATENT DOCUMENTS

| | | | |
|---|---|---|---|
| 5,705,369 | A | 1/1998 | Torget et al. |
| 5,766,159 | A | 6/1998 | Martin et al. |
| 5,866,242 | A | 2/1999 | Tan et al. |
| 5,902,454 | A | 5/1999 | Nelson |
| 6,045,545 | A * | 4/2000 | Vandemoortele et al. ............ 604/385.23 |
| 6,063,982 | A | 5/2000 | Martin et al. |
| 6,103,059 | A | 8/2000 | Call |
| 6,110,323 | A * | 8/2000 | Marsland .................. 162/14 |
| 6,162,961 | A | 12/2000 | Tanner et al. |
| 6,210,801 | B1 | 4/2001 | Luo et al. |
| 6,258,175 | B1 | 7/2001 | Lightner |
| 6,464,832 | B2 | 10/2002 | Engelhardt et al. |
| 6,506,283 | B2 * | 1/2003 | Henricson et al. ........... 162/246 |
| 6,533,896 | B1 | 3/2003 | Tikka et al. |
| 6,770,168 | B1 | 8/2004 | Stigsson |
| 2002/0017370 | A1 | 2/2002 | Henricson et al. |
| 2003/0093047 | A1 | 5/2003 | Nguyen |
| 2003/0145961 | A1 | 8/2003 | Rousu et al. |
| 2003/0183351 | A1 | 10/2003 | Sealey et al. |
| 2004/0020854 | A1 | 2/2004 | Ali et al. |
| 2004/0200589 | A1 * | 10/2004 | Herring et al. .................. 162/82 |
| 2005/0065336 | A1 | 3/2005 | Karstens |
| 2007/0193706 | A1 | 8/2007 | Kirov et al. |

FOREIGN PATENT DOCUMENTS

| | | |
|---|---|---|
| CA | 2368872 | 10/2000 |
| GB | 1434232 | 5/1976 |
| RU | 2037594 | 6/1995 |
| RU | 2045597 | 10/1995 |
| RU | 2090170 | 9/1997 |
| RU | 2121025 | 10/1998 |
| RU | 2127783 | 3/1999 |
| RU | 2220245 | 7/2003 |
| RU | 2002125519 | 3/2004 |
| RU | 2003111755 | 8/2004 |
| RU | 2248421 | 3/2005 |
| SU | 1606559 | 11/1990 |
| WO | 9425668 | 11/1994 |
| WO | 9508648 | 3/1995 |
| WO | 9739188 | 10/1997 |
| WO | 9947733 | 9/1999 |
| WO | WO 00/28133 | 5/2000 |
| WO | 0038607 | 7/2000 |
| WO | 0160752 | 8/2001 |
| WO | 0224032 | 3/2002 |
| WO | 03046227 | 6/2003 |
| WO | WO 2006/127880 | 11/2006 |

OTHER PUBLICATIONS

Syverud K. and Toven K., Swelling Properties of Sulphite Pulps, 2003, Norwegian Pulp and Paper research Institute, Figure 2 and Figure 3.*

Chritos L. and Prior B., Bleaching Response of Sulfite Pulps to Pretreatment with Xylanases, 1997, Biotechnol. Prog, vol. 13, Abstract.*

Obermanne H., A Study of the effect of Hemicelluloses on Beating and Strength of Pulps, Jun. 1934, Institute of Paper Chemistry, p. 51, 67-71.*

Ratliff F., The Possible Correlation Between Hemicelluloses and the Physical Properties of Bleached Kraft Pulps, Jun. 1948, Institute of Paper Chemistry, p. 69-76.*

Smook, Handbook for Pulp and Paper Technologists, 1992, Angus Wilde Publications, 2nd edition, p. 163.*

Pekarovicova Alexadra et al., Prebleaching kraft pulp by xylanases, the effect of water prehydrolysis,1992, TAPPI Journal vol. 76, No. 11, whole document.*

Gullichsen et al., Chemical Pulping 6A,1999, Fapet Oy,p. A658-659.*

Van Heiningen, Hemicellulose Extraction and Its Integration in Pulp Production (Part of the Quarterly Forest Products Industry of the Future Quarterly status report for Q1 05) [downloaded from www.p2pays.org], Van Heiningen report is dated Jan. 31, 2005 quarterly report availible Jun. 22, 2005 [downloaded online Oct. 6, 2008], Department of Energy, p. 53-63.*

Smook, Handbook for Pulp and Paper Technologists, 1992, Angus Wilde Publications, 2nd edition, Chapter 13.*

Gullichsen et al., Chemical Pulping 6A, 1999, Fapet Oy, p. A573-A574.*

Archive.org, evidence of public availibility of Van Heiningen reference on Mar. 9, 2005 [downloaded online Sep. 29, 2009].*

Smook, Handbook for Pulp and Paper Technologists, 1992, Angus Wilde Publications, 2nd edition, chapter 15.*

Smook, Handbook for Pulp and Paper Technologists, 1992, Angus Wilde Publications, 2nd edition, chapter 7.*

Gullichsen editor, Chemical Pulping 6A, 1999, Fapet Oy,p. A635-A665.*

Handbook for Pulp & Paper Technologies, 2nd Edition, G.A. Smook, Angus Wilde Publications, 1992.

Gullichsen, J. Editor, Chemical Pulping, 1999, Fapet Oy., p. A25-A28.

Durbak Irene, Dissolving Pulp Industry, Sep. 1993, Forest Product Labratory, p. 1-3.

Smook, Handbook for Pulp and Paper Technologiests, 1992 Angus Wilde Publication, 2nd edition, p. 163.

Pekarovicova Alexadra et al., Prebleaching kraft pulp by xylanases, the effect of water prehydrolysis, 1992 TAPPI Journal vol. 76, No. 11, whole document.

Smook, Handbook for Pulp and Paper Technologists, 1992, Angus Wilde Publications, 2nd edition, p. 100, 194, and 206.

Smook, Handbook for Pulp and Paper Technologists, 1992, Angus Wilde Publications, 2nd edition, chapter 9, pp. 98-132.

Rydholm, Pulping Processes, 1965, Interscience Publishing, p. 663-671, 715, 1122-1125.

* cited by examiner

MODIFIED KRAFT FIBERS

RELATED PATENT APPLICATIONS

This is a non-provisional application which claims priority from U.S. Provisional Patent Application Ser. No. 60/684,018 filed on May 24, 2005.

FIELD OF THE INVENTION

This invention relates to an improved method for manufacturing pulp, pulp manufactured in accordance with this process and paper and paperboard products manufactured from the bleached pulp of this invention. More particularly, this invention relates to improvement in processes for the manufacture of pulps having reduced hemicellulose content which exhibit one or more beneficial properties.

BACKGROUND OF THE INVENTION

Processes for digesting wood chips to form pulps and processes of bleaching pulps and using bleached pulps in the manufacture of paper, paperboard and absorbent products are known. See for example U.S. Pat. Nos. 6,063,982; 5,766,159; 5,902,454 and 6,464,832

SUMMARY OF THE INVENTION

One aspect of this invention relates to a method of producing a modified Kraft pulp for use in paper or paper web products comprising:

treating wood chips with a liquid comprising water in an extraction process to remove hemicellulose to form treated wood chips; and subjecting said treated wood chips to kraft pulping to form a modified Kraft pulp wherein the amount of hemi cellulose contained in the modified Kraft pulp is from about 5 to about 10% by dry weight of the modified pulp.

Another aspect of this invention relates to modified Kraft pulp formed by the process of this invention. The modified Kraft pulp of this invention exhibits one or more advantages. These advantages include improved drainage which enhances the speed of paper making processes which use the pulp of this invention as compared to unmodified pulps. Such advantages also include higher freeness and enhanced bleachability, drainage, dewatering and/or drying as compared to the un-modified Kraft pulp.

Yet another aspect of this invention relates to paper, paperboard and absorbent products prepared from the modified pulp of this invention. Such products exhibit higher bulk as compared to such products formed from unmodified pulps.

Still another aspect of this invention relates to a personal hygiene article for absorbing fluids, the article comprising at least one fluid permeable top sheet layer and at least one substantially fluid impermeable back sheet layer; and
an absorbent sub layer material interposed between the top sheet layer and the back sheet layer, the sub layer material comprising modified pulp of this invention.

DETAIL DESCRIPTION OF THE INVENTION

Figure 1:
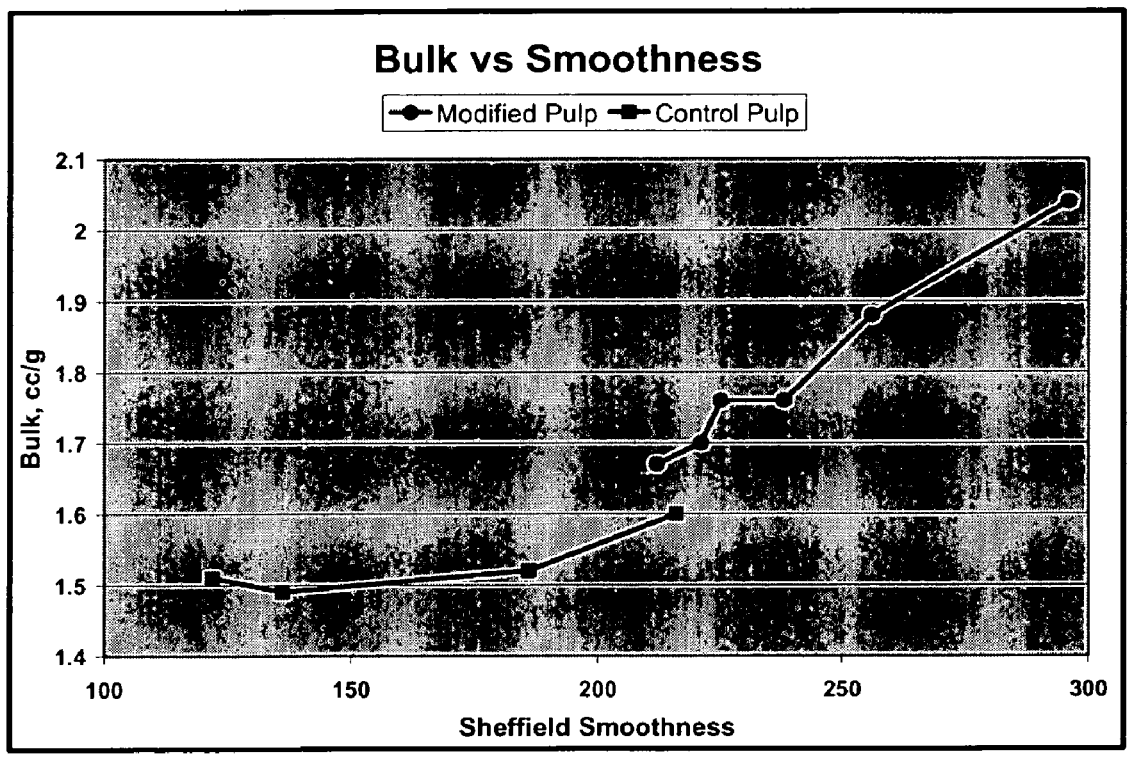
FIG. 1 is a plot of water retention versus freeness for the modified pulp of this invention and the same unmodified pulp.

In the first step of the process of this invention wood chips are extracted with a liquid comprising water to reduce and to remove hemicellose to form treated wood chips. The type of wood chips used in the process of this invention is not critical and any such material can be used. For example, useful wood chips include those derived from hardwood trees, softwood trees, or a combination of hardwood and softwood trees. The term "hardwood pulps" as used herein refers to fibrous pulp derived from the woody substance of deciduous trees (angiosperms) such as aspen and maple, whereas "softwood pulps" are fibrous pulps derived from the woody substance of coniferous trees (gymnosperms) such as southern pine.

The wood chips are extracted with a composition comprising water. The liquid can consist of water alone or may include one or more additional materials which enhance the extraction of the hemicellulose. Such additional materials which enhance the extraction of hemicellulose may vary widely and include inorganic bases such as sodium hydroxide, potassium hydroxide and ammonium hydroxide. Sodium hydroxide is preferred for use in the practice of this invention.

In the preferred embodiments of this invention the wood chips are treated with an aqueous base solution having a pH greater than 7. Use of the aqueous base solution allows the extraction to be carried out at lower temperatures as for example at room or ambient temperatures with shorter extractions. The pH of the aqueous base solution is preferably equal to or greater than about 8, more preferably from about 8 to about 12 and most preferably from about 9 to about 11.

Treatment temperatures may vary widely and any temperature sufficient to form the desired treated wood chips can be used. The treatment temperature is usually at least about 20° C. although lower temperatures may be used if effective to provide the desired treated wood chips. The treatment temperature is preferably from about 20° C. to about 120° C., more preferably from about 40° C. to about 120° C. and most preferably from about 40° C. to about 90° C., with a temperature of from about 60° C. to about 90° C. being the temperature in the embodiments of choice.

Treatment times may vary widely and any time sufficient to form the desired treated wood chips can be used. The treatment time is usually at least about 5 minutes although longer treatment times may be used if effective to provide the desired ligno cellulosic material. The treatment time is preferably from about 5 minutes to about 20 hours, more preferably 15 minutes to about 10 hours and most preferably from about 30 minutes to about 4 hours.

Hemicellulose removed from the wood chips in the first step of this invention can vary widely provided that the amount remaining in the modified pulp after Kraft pulping in the second step of the process of this invention is from about 5% to about 10% by dry weight of the modified pulp. For example, the amount of hemicellulose removed in the first step may vary from about 5 by weight or lower to about 20% by weight or higher based on the total amount of hemicellulose in the wood chips. In the preferred embodiments of the invention, the amount of hemicellulose removed in the first step may vary from about 10% by weight to about 15% by weight based on the total amount of hemicellulose in the wood chips.

The extracted hemicelluloses can be diverted away from the pulping process stream, thus reducing the Kraft black liquor recovery boiler heat load (usually being the production capacity bottle-neck). The extracted hemicelluloses can be burned in the hog boiler or other types of biomass boilers, such as by spraying onto the biomass fuel feedstock (barks, pin chips, sawdust, coal, etc.), and therefore maintaining the energy balance in the mill. Alternatively, the extracted hemicelluloses can be used as feedstock for fermentation to produce fuel chemicals. The extracted hemicelluloses can be oxidized, or derivatized with ether functional groups or cationic charges. The hemicelluloses thus treated can then be used as papermaking additives, such as added in the papermachine wet end, or mixed with starch for the use in sizepress, or coating.

The second step of the process of this invention the treated or extracted wood chips are subject to a chemical or semi chemical pulping process. Such processes are well known to those of skill in the art and will not be described in any great detail. See for example "Handbook for Pulp & Paper Technologies", $2^{nd}$ Edition, G. A. Smook, Angus Wilde Publications (1992) and references cited therein, all of which are herein incorporated by reference. Illustrative of useful chemical and semi-chemical pulping processes are carbonate pulping processes, green liquor pulping processes, Kraft pulping processes or Sulfite pulping processes. Kraft pulping is preferred for use in the practice of this invention.

The amount of hemicellulose contained in the modified Kraft pulp is from about 3 to about 15% by dry weight of the modified pulp. The amount of hemicellulose contained in the modified Kraft pulp is preferably from about 4 to about 13% by dry weight of the modified pulp. The amount of hemicellulose contained in the modified Kraft pulp is more preferably from about 5 to about 10% by dry weight of the modified pulp and is most preferably from about 6 to about 8% by dry weight of the modified pulp. This modified Kraft pulp (either hardwood or softwood) displays significantly higher brightness and paper bulk with improved drainage and drying potential, as compared to the unmodified pulp.

In a preferred embodiment of this invention, the modified Kraft pulp of this invention contains at least about 1% by weight less hemicelluloses of the same pulp when un-modified. In these preferred embodiments of the invention, the modified Kraft pulp contains from about 1% to about 20% by weight less hemicelluloses than the same pulp when un-modified. In these preferred embodiments of the invention, the modified Kraft pulp contains from about 1% to about 20% by weight less hemicelluloses than the same pulp when un-modified. In these preferred embodiments of the invention, the modified Kraft pulp preferably contains from about 1% to about 16% by weight less hemicelluloses than the same pulp when un-modified. In these preferred embodiments of the invention, the modified Kraft pulp more preferably contains from about 2% to about 16% by weight less hemicelluloses than the same pulp when un-modified. In these preferred embodiments of the invention, the modified Kraft pulp most preferably contains from about 2% to about 8% by weight less hemicelluloses than the same pulp when un-modified In the preferred embodiments of the invention the modified pulp of this invention exhibits higher freeness and better drainage than the un-modified pulp. The increase in freeness is preferably at least about 20 CSF units greater than that of the un-modified pulp. In the more preferred embodiments of the invention the increase in freeness is at least about 50 CSF units greater than that of the un-modified pulp and in the most preferred embodiments of the invention the increase in from about 50 to about 200 CSF units greater than that of the un-modified pulp.

In the preferred embodiments of the invention the modified pulp of this invention exhibits reduced water retention values (WRV) as compared to the unmodified pulp. In these preferred embodiments of the invention the decrease in water retention value is preferably greater than about 0.1 g/g. In the more preferred embodiments of the invention the decrease in water retention is preferably greater than about 0.2 g/g. and in the most preferred embodiments of the invention decrease in water retention is from about 0.2 to about 0.5 g/g.

The Kappa Number of the pulp can vary widely. The Kappa number is preferable form about 15 to about 28 and is more preferably from about 23 to about 26.

The modified pulp of this invention can be subjected to one or more post pulping treatments as for example beaching with convention bleaching agents such as chlorine dioxide, elemental chlorine, ozone and peroxide using procedures and apparatuses described in "Handbook For Pulp & Paper Technologies", $2^{nd}$ Edition, G. A. Smook, Angus Wilde Publications (1992) and references cited therein. The pulp can also be subjected to extraction as for example oxygen delignification or extraction with base preferably in the presence of peroxide. In the preferred embodiments of the invention, the modified pulp of this invention exhibits improved bleachability. A benefit of improved bleachability is that the amount of bleaching chemical dose (kappa factor) used can be reduced while reaching the same brightness as the un-modified bleached pulp, thus generating chemical cost savings. Another benefit of improved bleachability is the same amount of bleaching chemical as the un-modified pulp case can be used, especially in early bleaching stages, thus reducing the number of bleaching stages (savings in capital and energy) required to reach the same brightness. Yet another benefit of improved bleachability is that very high brightness pulp can be produced, which cannot be practically achieved with un-modified pulp. For instance, it is well-known fact that Kraft pulp cannot be bleached practically beyond the brightness ceiling of 90 ISO brightness. With this modified Kraft pulp, however, very high brightness levels of 90-95 ISO brightness can be achieved in the preferred embodiments of the invention with practical amount of bleaching chemicals.

In other preferred embodiment of this invention the modified pulp has less anionic charge or less hydrated fiber surface, showing better affinity for paper chemicals such as sizing, dyes and optical brighteners. In another preferred embodiment of this invention the modified Kraft pulp, containing less hemicellulose, has less moisture sensitivity and shows improved performance in hydroexpansivity.

The modified pulp of this invention can also be used in the manufacture of paper and packaging products such as printing, writing, publication and cover papers and paperboard products. Illustrative of these products and processes for their manufacture are those described in U.S. Pat. Nos. 5,902,454 and 6,464,832.

In paper or paperboard making process, the modified pulp of this invention can be used with no or little refining, or the modified pulp can be mixed with fully-refined unmodified pulps, especially softwood pulps, prior to use in paper or paperboard manufacture. The modified pulp of this invention or pulp mixtures comprising the modified pulp of this invention is formulated into an aqueous paper making stock furnish which also comprises one of more additives which impart or enhance specific sheet properties or which control other process parameters. Illustrative of such additives is alum which is used to control pH, fix additives onto pulp fibers and improve retention of the pulp fibers on the paper making machine. Other aluminum based chemicals which may be added to the furnish are sodium aluminate, poly aluminum silicate sulfate and poly aluminum chloride. Other wet end chemicals which may be included in the paper making stock furnish for conventional purposes are acid and bases, sizing agents, dry-strength resins, wet strength resins, fillers, coloring materials, retention aids, fiber flocculants, defoamers, drainage aids, optical brighteners, pitch control chemicals, slimicides, biocides, specialty chemicals such as corrosion inhibitors, flame proofing and anti-tarnish chemicals, and the like. Methods and procedures for formulating mechanical bleached pulp, aluminum based wet end chemicals and other optional wet end chemicals are well known in the art and will not be described in any great detail. See for example, "Handbook For Pulp & Paper Technologies", $2^{nd}$ Edition, G. A. Smook, Angus Wilde Publications (1992) and references cited therein, all of which are herein incorporated by reference.

The aqueous paper making stock furnish comprising the bleached mechanical pulp and the aluminum based compounds is deposited onto the forming wire of a conventional paper making machine to form a wet deposited web of paper or paperboard and the wet deposited web of paper or paperboard is dried to form a dried web of paper or paperboard. Paper making machines and the use of same to make paper are well known in the art and will not be described in any great detail. See for example, *Handbook For Pulp & Paper Technologies*, supra. By way of example, the aqueous paper making stock furnish containing pulp, aluminum based and other optional additives and usually having a consistency of from about 0.3% to about 1% is deposited from the head box of a suitable paper making machine as for example a twin or single wire Fourdrinier machine. The deposited paper making stock furnish is dewatered by vacuum in the forming section. The dewatered furnish is conveyed from the forming section to the press section on specially-constructed felts through a series of roll press nips which removes water and consolidates the wet web of paper and thereafter to the dryer section where the wet web of paper is dried to form the dried web of paper of this invention. After drying, the dried web of paper may be optionally subjected to several dry end operations such as and various surface treatments such as coating, and sizing and calendering.

In the preferred embodiments of this invention modified pulp forms paper products which exhibit a bulk which is greater than that exhibited by the same or substantially the same pulp when unmodified. In these preferred embodiments of the invention modified pulp forms paper products which exhibit a bulk which is at least about 2% greater than that exhibited by the same or substantially the same pulp when unmodified. In these preferred embodiments of the invention modified pulp forms paper products which exhibit a bulk which is preferably at least about 5% greater than that exhibited by the same or substantially the same pulp when unmodified. In these preferred embodiments of the invention modified pulp forms paper products which exhibit a bulk which is more preferably from about 5% to about 40% greater than that exhibited by the same or substantially the same pulp when unmodified. In these preferred embodiments of the invention modified pulp forms paper products which exhibit a bulk which is most preferably from about 5% to about 30% greater than that exhibited by the same or substantially the same pulp when unmodified.

The paper manufactured in accordance with this invention can be used for conventional purposes. For example, the paper is useful as printing paper, publication paper, newsprint and the like.

For example the modified pulp of this invention can be used prepared absorbent articles as for example diapers, tissues, towels, personal hygiene products using conventional processes. Such products and their methods of manufacture are known to those of skill in the art and will not be described in detail. See for example, U.S. Pat. Nos. 6,063,982 and 5,766,159 and references described therein. The modified pulp of this invention can be used to make saturating kraft paper.

Saturating kraft paper is a paper sheet made from unbleached kraft pulp (mixture of mostly hardwood and some softwood such as southern pine) that is used as substrate for impregnation and curing with resin polymers. Saturating kraft paper is used as home and office building materials, such as kitchen counter tops.

The present invention will be described with references to the following examples. The examples are intended to be illustrative and the invention is not limited to the materials, conditions or process parameters set forth in the examples.

Example 1

Northern hardwood chips (predominantly maple), was extracted with water at 160° C. degrees to effect 19% material removal. The extracted chips was then cooked by Kraft pulping to Kappa number 25. As control, the un-extracted chips was also Kraft cooked to reach a target Kappa number of 25. Both the treated pulp and the control pulp were bleached by the sequences as shown in Table I below.

TABLE I

| | Bleaching Sequences |
|---|---|
| Brown stock | Extracted/Kraft-cooked-kappa 25; Control/Kraft-cooked-kappa 25 |
| Do stage | Kappa factor 0.08 for treated pulp (0.76% ClO2 applied on pulp) |
| | Kappa factor 0.08 for control pulp (0.76% ClO2 applied) |
| | Kappa factor 0.14 for control pulp (1.33% ClO2 applied) |
| | 40 minutes at 50 C., consistency 4% |
| Eop stage | 90 minutes at 75 C., consistency 10%, 0.4% H2O2 applied, 1.36% NaOH applied, O2 pressure 60 psi. |
| D1 stage | 3 hours at 62 C., consistency 10%, 0.73% ClO2 applied, 0.3% NaOH applied on pulp. |
| Ep stage | 60 minutes at 75 C., consistency 10%, 0.16% H2O2 applied, 0.46% NaOH applied on pulp. |
| D2 stage | 3.5 hours at 78 C., consistency 10%, 0.21% ClO2 applied on pulp. |

The brightness results are set forth in Table II below.

| | Brightness | | |
|---|---|---|---|
| | Treated Pulp-Kappa factor 0.08 in Do | Control Pulp-Kappa factor 0.08 in Do | Control Pulp-Kappa factor 0.14 in Do |
| Brown stock | 28.2 | 21.4 | 21.4 |
| After Do | 35.1 | 26.3 | 36.5 |
| After Eop | 62.1 (P#3.3) | 40.3 (P#7.1) | 59.2 (P#4.1) |
| After D1 | 84.1 | 68 | 80.5 |
| After Ep | 87.5 | 70.8 | 83.9 |
| After D2 | 91.8 | 82.4 | 89.5 |

It is obvious that the treated pulp can be bleached much easily. In this example, the savings in ClO2 dose is more than 11 lb per ton of pulp production. This is very significant economical benefit. Moreover, this also indicates that if a "normal" dose of ClO2 is used in the Do stage (i.e., kappa factor of 0.14 to 0.2) for the modified Kraft pulp, a very high brightness pulp (much above the traditional pulp brightness ceiling of ~90) can be made. In fact, a very high brightness pulp can be used in the manufacture of high brightness papers and saving optical brightener usage.

Example 2

The modified pulp and the control pulp, which had been bleached with the same dose of ClO2 bleaching chemicals as in Example 1, were refined to various level of freeness. The water retention values, bulk and smoothness were evaluated. The results are set forth in Table III below and in FIGS. 1 and 2.

TABLE III

| | Freeness, csf | Water Retention Value, g/g | Bulk, cc/g | Sheffield Smoothness |
|---|---|---|---|---|
| Modified Pulp | 575 (unrefined) | 1.59 | 2.04 | 296 |
| | | — | 1.88 | 256 |
| | 558 | 1.7 | 1.76 | 238 |
| | 493 | 1.74 | 1.76 | 225 |
| | 476 | 1.77 | 1.70 | 221 |
| | 463 | 1.72 | 1.67 | 212 |
| | 432 | | | |
| Control Pulp | 445 (unrefined) | 1.95 | 1.60 | 216 |
| | | 2.09 | 1.52 | 186 |
| | 315 | 2.17 | 1.49 | 136 |
| | 220 | 2.38 | 1.51 | 122 |
| | 206 | | | |

Freeness and water retention values are indications of paper drainage and dewatering. As shown in FIG. 1, the data shows that the modified pulp may be dewatered and dried faster on paper-machine than the unmodified pulp.

Figure 2:
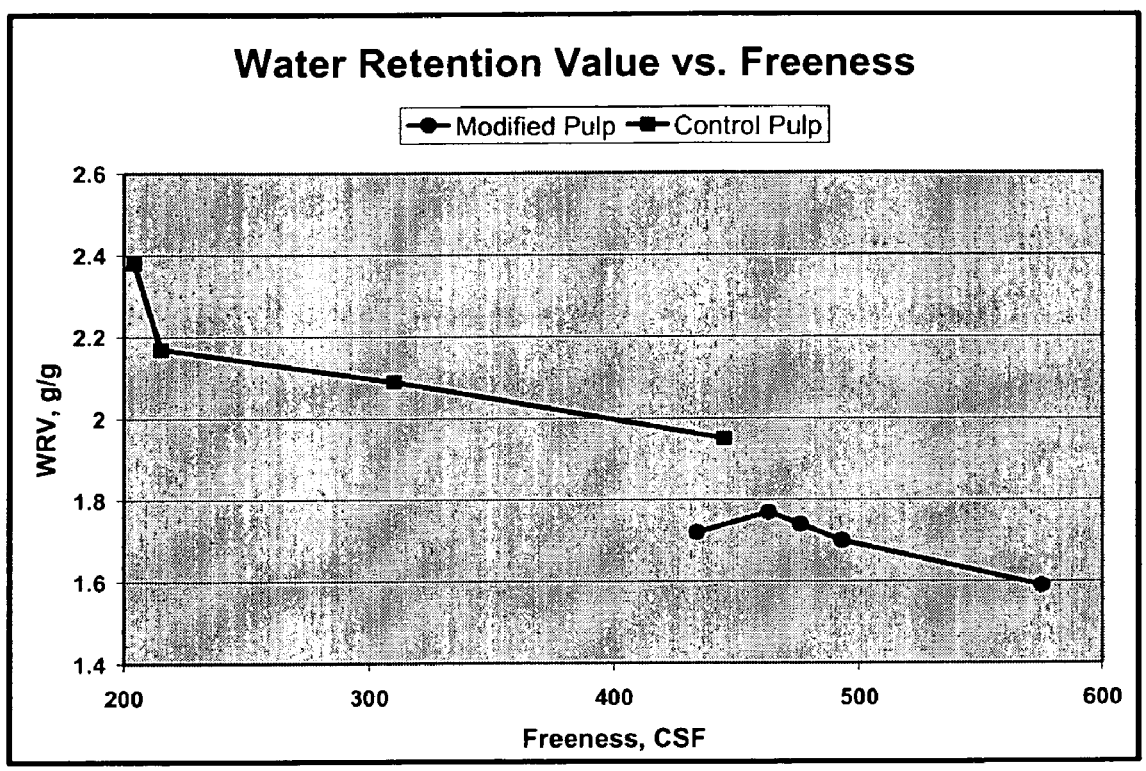
FIG. 2 is a plot of bulk versus Sheffield Smoothness for the modified pulp of this invention and the same unmodified pulp.

The data also demonstrates that the paper bulk is significantly improved. As shown in FIG. 2, this is even true when comparing the bulk increase at the same smoothness of paper.

Example 3

Modified Kraft pulp was also made from Southern Pine chips. Like the hardwood case, significant bleaching savings was obtained. Table IV below indicates the reduced fiber coarseness of the modified pulp vs. the control pulp at the same kappa number of 26. The test was done by Kajaani FiberLab tester.

TABLE IV

| | Modified Pine | Control pine |
|---|---|---|
| Fiber Coarseness, mg/100 m | 26.1 | 29.2 |

Example 4

Bleached southern hardwood Kraft pulp was treated with NaOH solution (the concentration of NaOH being 5% based on the total system of pulp and water) at ambient temperature for 15 minutes. This is an alternative way of extracting hemicelluloses from the fibers. The pulp was then thoroughly washed with water, and made into Tappi hand-sheets. Paper bulk of paper formed from the modified pulp was 2.03 cc/g, while the control paper bulk was 1.85 cc/g. The brightness was also increased from the control of ISO 86.4 to the modified pulp of ISO 89.2.

What is claimed is:
1. A method of producing a modified bleached Kraft pulp for use in paper or paper web products, the method comprising:
   treating wood chips with an alkaline solution in an extraction process to remove 5% to 20% hemicellulose to provide extracted hemicellulose and to form a treated wood chips under caustic condition;
   subjecting said treated wood chips to Kraft pulping to form a modified Kraft pulp wherein the amount of hemicellulose contained in the modified Kraft pulp is from more than 4% to up to and including about 9% by oven dried weight of the modified Kraft pulp; and
   after the subjecting step, bleaching the modified Kraft pulp to form a modified bleached Kraft pulp having an ISO brightness of at least 80; and
   after bleaching, manufacturing paper, paperboard, or fluff pulp using a pulp composition comprising the modified bleached Kraft pulp; and
   wherein the extracted hemicellulose is oxidized or derivatized with ether functional groups or cationic charges and then added to a size press or coater of a papermaking process.

2. The method of claim 1 wherein the amount of hemicellulose contained in the modified Kraft pulp is from about 5% to about 9% by oven dried weight of the modified Kraft pulp.

3. The method of claim 2 wherein the amount of hemicellulose contained in the modified Kraft pulp is from about 6% to about 9% by oven dried weight of the modified Kraft pulp.

4. The method of claim 3 wherein the amount of hemicellulose contained in the modified Kraft pulp is from about 7% to about 9% by oven dried weight of the modified Kraft pulp.

5. The method of claim 1 wherein the modified Kraft pulp exhibits water retention value of from about 0.2 g/g less than that of the same or substantially the same unmodified Kraft pulp.

6. The method of claim 1 wherein the modified Kraft pulp exhibits water retention value of from about 0.2 g/g to about 0.5 g/g less than that of the same or substantially the same unmodified Kraft pulp.

7. The method of claim 1 wherein the modified Kraft pulp exhibits freeness of at least about 20 CSF units greater than that of the same or substantially the same unmodified Kraft pulp.

8. The method of claim 7 wherein the modified Kraft pulp exhibits freeness of at least about 50 CSF units greater than that of the same or substantially same un-modified Kraft pulp.

9. The method of claim 7 wherein the modified Kraft pulp exhibits freeness of from about 50 to about 200 CSF units greater than that of the same or substantially same un-modified Kraft pulp.

10. The method of claim 1 wherein the modified Kraft pulp exhibits higher bulk gain ranges from 0.05 cc/g to 0.5 cc/g.

11. The method of claim 10 wherein the modified Kraft pulp exhibits higher bulk gain ranges from 0.1 cc/g to 0.5 cc/g.

12. The method of claim 1 wherein the bleached modified Kraft pulp exhibits an ISO brightness gain from about 5 to about 15 points when compared to an unmodified Kraft pulp in which an equal amount of bleaching chemical is used for respective modified Kraft pulp and un-modified Kraft pulp.

13. The method of claim 12 wherein the bleached modified Kraft pulp exhibits ISO brightness ranges from 80 to 95 when compared to the unmodified Kraft pulp and further uses about 5 lbs to about 15 lbs per ton less of bleaching chemical.

14. The method of claim 1 further comprising a washing step.

15. The method of claim 1 further comprising a refining step.

16. A method of producing a modified bleached Kraft pulp for use in paper or paper web products, the method comprising:
   treating wood chips with an alkaline solution in an extraction process to remove 5% to 20% hemicellulose to provided extracted hemicellulose and to form a treated wood chips under caustic condition;

subjecting said treated wood chips to Kraft pulping to form a modified Kraft pulp wherein the amount of hemicellulose contained in the modified Kraft pulp is from more than 4% to up to and including about 9% by oven dried weight of the modified Kraft pulp;

after the subjecting step, washing the modified Kraft pulp to remove Kraft liquor therefore; and after the washing step, bleaching the modified Kraft pulp to form a modified bleached Kraft pulp having an ISO brightness of at least 80; and after bleaching, manufacturing paper, paperboard, or fluff pulp using a pulp composition comprising the modified bleached Kraft pulp; and wherein the extracted hemicellulose is oxidized or derivatized with ether functional groups or cationic charges and then added to a size press or coater of a papermaking process.

17. A method of producing a modified bleached Kraft pulp for use in paper or paper web products, the method comprising:

treating wood chips with an alkaline solution in an extraction process to remove 5% to 20% hemicellulose to provide extracted hemicellulose and to form a treated wood chips under caustic condition; subjecting said treated wood chips to Kraft pulping to form a modified Kraft pulp wherein the amount of hemicellulose contained in the modified Kraft pulp is from more than 4% to up to and including about 9% by oven dried weight of the modified Kraft pulp;

after the subjecting step, washing the modified Kraft pulp to remove the Kraft liquor therefrom; and after the washing step, bleaching the modified Kraft pulp to form a modified bleached Kraft pulp having an ISO brightness of at least 80;

after the bleaching step, refining the modified bleached Kraft pulp; and after bleaching, manufacturing paper, paperboard, or fluff pulp using a pulp composition comprising the modified bleached Kraft pulp; and wherein the extracted hemicellulose is oxidized or derivatized with ether functional groups or cationic charges and then added to a size press or coater of a papermaking process.

\* \* \* \* \*